United States Patent [19]

Schmidt

[11] Patent Number: 5,422,074
[45] Date of Patent: Jun. 6, 1995

[54] METHODS FOR TREATING INFECTIOUS WASTES

[75] Inventor: Erick Schmidt, Edmonton, Canada

[73] Assignee: Envirotrust Technologies, Inc., Toronto, Canada

[21] Appl. No.: 92,660

[22] Filed: Jul. 15, 1993

Related U.S. Application Data

[63] Continuation of Ser. No. 785,660, Oct. 31, 1991, abandoned.

[51] Int. Cl.$^6$ .............................................. A61L 2/00
[52] U.S. Cl. ...................................... 422/28; 422/27; 422/32; 422/33; 588/258; 588/901
[58] Field of Search ..................... 422/27, 28, 32, 33; 588/258, 901; 134/22.16, 25.1, 42, 606, ; 241/606; 71/64.03, 64.13, 3,6, 44, 47

[56] References Cited

U.S. PATENT DOCUMENTS

| | | | |
|---|---|---|---|
| Re. 11,941 | 10/1901 | Thomson . | |
| 1,961,740 | 6/1934 | Conquest | 134/22.16 X |
| 3,591,416 | 7/1971 | Johnson | 134/22.16 X |
| 3,767,362 | 10/1973 | Griffin et al. | 21/58 |
| 3,953,191 | 4/1976 | Barton | 71/23 |
| 3,976,465 | 8/1976 | O'Donnell | 71/13 |
| 4,050,388 | 9/1977 | Boyd | 110/8 P |
| 4,117,175 | 9/1978 | Senior | 426/657 |
| 4,179,347 | 12/1979 | Krause et al. | 204/149 |
| 4,743,287 | 5/1988 | Robinson | 71/12 |
| 4,954,316 | 9/1990 | Colobus | 422/37 |
| 5,021,077 | 6/1991 | Moore | 71/17 |
| 5,080,721 | 1/1992 | Flanigan et al. | 134/26 |
| 5,087,420 | 2/1992 | Jackson | 422/37 |
| 5,089,228 | 2/1992 | Meijer | 422/37 |
| 5,135,664 | 4/1992 | Burnham | 210/751 |
| 5,190,725 | 2/1993 | Meijer et al. | 422/37 |
| 5,275,733 | 1/1994 | Burnham | 210/609 |

OTHER PUBLICATIONS

Block, Seymor S. *Disinfection, Sterilization and Preservation*, pp. 660-661 814, 1983.

*The EPA Guide for Infectious Waste Management*, Chap. 4, U.S. Dept. of Commerce, National Technical Information Service (1896).

Straub, F. G. (1942), "Solubility of Salts in Steam at High Pressures", Proceedings of III Annual Water Conference, Pittsburgh, Pa. pp. 31-43.

Tatarinov, B. P., et al., (1966), "Solubility of chlorides in Saturated Steam", Thermal Engineering, 13, 77-80.

Jonas, O. et al. (1979), "Turbine Steam Purity-1979 Update", Proc. 39th Int. Water Conf., (Pittsburgh), pp. 595-607.

Khaibullin, I.Kh., (1979), "Phase Diagrams for Steam Solutions and Caloric Properties of Two-and Three-Component System: $H_2O$-NaCl, $H_2O$-$Na_2SO_4$ and $H_2O$-NaCl-$Na_2SO_4$", Conference on Properties of Water and Steam, Munich 1979, pp.641-647.

Pocock, F. J., (1979?), "Understanding the Turbine Steam Environment", Babcock & Wilcox Company, Alliance Research Center, Alliance Ohio, pp.563-581.

Allmon, W. E., et al., (1983), "Deposition of Corrosive Salts from Steam", EPRI Rpt. RP 1068-1, Babcock & Wilcox Research Center, Alliance, Ohio.

Passell, T. O., Ph.D. (EPRI Project Manager), "Report Summary" Feasibility Study of *In Situ* Corrosive Salt Deposition Analysis, EPRI Project RP-1068-4, (1984), Prepared by Lockheed Palo Alto Research Laboratory, Palo Alto, Calif., (4 pages).

Roger, L. B., (1984), "Solubility of Corrosive Salts in Dry Steam", EPRI Report RP 969 (cover page, Abstract).

Sourirajan, S., G. C. Kennedy, (1962), "The System of $H_2O$-NaCl at Elevated Temperatures and Pressures", *Amer. J. Science*, 260, 115-141.

*Primary Examiner*—Robert J. Warden
*Assistant Examiner*—Krisanne M. Thornton
*Attorney, Agent, or Firm*—Panitch Schwarze Jacobs & Nadel

[57] ABSTRACT

Waste materials containing pathogenic microorganisms may be processed by a method that includes granulating the waste material; treating the granulated waste material by heating at a temperature of about 160° to about 200° C. at a pressure of about 90 to about 226 psi in an atmosphere of the steam from a non-isotonic salt solution. The treatment is conducted for a period of time sufficient to substantially reduce the amount of pathogenic microorganisms present in the waste material. After treatment, the material is separated into useful solid and liquid phases.

18 Claims, 1 Drawing Sheet

METHODS FOR TREATING INFECTIOUS WASTES

This application is a continuation of application Ser. No. 07/785,660 filed Oct. 31, 1991, now abandoned.

FIELD OF THE INVENTION

The present invention is directed to methods for the treatment of biomedical and other infectious wastes. More specifically, the present invention is directed to methods for processing wastes containing pathogenic microorganisms to substantially reduce or eliminate the amount of pathogens present therein and to generate safer, industrially useful products.

BACKGROUND OF THE INVENTION

Various methods for treating or processing waste containing infectious material, i.e., waste containing various pathogenic microorganisms, are known in the art, and various technologies have been tested in attempts to effectively sterilize such wastes. However, the known, conventional processes have inherent disadvantages which limit their use.

The currently most widely used method of sterilizing or treating infectious wastes utilize thermal degradation as the primary treatment mechanism. The elevated temperatures used in these processes are generally achieved through dry air, steam or flame in order to sterilize infectious microorganisms by partial molecular degradation at lower temperatures or total molecular destruction at high temperatures.

An example of this type of method is the autoclave, which uses a combination of vacuum and pressurized steam to treat clinical products, such as instruments and containers, as well as to decontaminate post-patient care materials prior to disposal. The limitations of such sterilization systems include the possible escape of aerosolized and liquid borne pathogens through the drain and exhaust-ports of the system; the incomplete sterilization of materials containing pathogens resistant to the temperatures used; possible inadequate steam penetration to the center of the waste load; and the continuing requirement of storing, transporting and disposing the treated material, generally utilizing further incineration or landfills. Thus, this technology creates a secondary environmental problem relating to the disposal of the treated waste and is not designed to create any useful by-products from the treated materials.

Another conventional process utilizing thermal technology is incineration, which is presently the most commonly used infectious waste treatment method in the world. However, this technology is now coming under severe environmental criticism, and is subject to strict regulatory standards. In many instances, incineration is being banned entirely because of the likelihood that hazardous products are generated thereby. Thus, new guidelines regarding incineration involve higher standards relating to emissions, such as hydrogen chloride and carbon monoxide, and new requirements relating to dioxins and furans produced from burning complex plastic materials, such as polyesters. In order to comply with these standards, conventional incineration technology must be re-designed significantly, making these treatment methods economically unfeasible. The problems resulting from potential toxic emissions from incineration processes are an additional limitation to the traditional problems of intermediate storage and transport associated with this process, as well as the disposal of the residual ash in landfills.

A third conventional method of treating infectious waste which employs thermal technology comprises heating the waste in large scale microwave systems. Microwave systems are particularly effective for sterilizing water-based tissue and materials which allow the absorption of microwave frequencies. However, microwave systems have been found to be ineffective for achieving thermal sterilization of dry matter. Moreover, microwave methods do not penetrate materials shielded by metallic enclosures, such as needles, syringes, etc. Such processes are also expensive for large volume treatment and produce disinfected waste which requires further disposal, with its accompanying costs and problems.

Waste treatment processes employing the use of chemicals are also known and used in the art. In general, there are two major chemical methodologies utilized in waste treatment systems, utilizing both gas and liquid mechanisms. An example of a gaseous system comprises contacting the waste load with an appropriate amount of a gaseous chemical agent such as ethylene oxide, formaldehyde, peracetic acid and beta-propyl acetone in an appropriate treatment vessel, such as an atmospheric chamber. Ethylene oxide gas is widely used in the sterilization of thermolabile materials, which would otherwise be damaged by exposure to heat and moisture. However, these treatment processes have fallen into disfavor since the chemicals used are considered to be probable human carcinogens and require extreme care and containment during use. These materials also remain hazardous after treatment and require special detoxification procedures so that their concentration in the treatment area meets safety standards.

Waste treatment methodology employing liquid chemicals comprises the use of chlorine which is a very strong oxidizing agent and reacts in water to form hypochlorite ions. An example of a treatment methodology employing liquid chlorine comprises granulating the waste material and then subjecting the granulated particles to a chlorine spray or bath treatment. The chlorine treatment disinfects the granulated waste material by oxidizing the pathogens. However, such systems have limitations relating to the drying and final disposal of the chlorinated disinfected wastes, the safe disposal of the residual chlorinated treatment solution and the comprehensiveness of the exposure and subsequent inactivation of all pathogens embedded in the waste mass.

More recent, emerging infectious waste treatment processes employ advanced technologies originating from the fields of electronics and physics. Such processes achieve the destruction of infectious microorganisms within the waste by bombarding the waste load with electron beams or electromagnetic radiation. Examples of such methodology presently in use employ gamma radiation, electron beam radiation and ultraviolet radiation to destroy the pathogens present in the waste load.

For example, gamma irradiation systems utilize powerful radiation originating from radioactive sources such as Cobalt-60 and Cesium-137. Such systems are primarily used for the sterilization of medical supplies and food. However, recent high power gamma irradiation systems have been designed to treat large volumes of infectious waste materials in continuous conveyorized facilities. The disadvantages of such systems include the obvious hazards to personnel which require extra safety measures, such as shielding of the radiation units, which ultimately decreases the cost efficiency of these methods. Moreover, the effectiveness of such processes are dependent on the continual adjustment of exposure durations in order to accommodate for the continuous decay of the radioactive material. A more serious problem of these systems relates to the disposal of the spent radiation sources and the treated waste due to the existence of trace radioactivity therein.

Another treatment comprises subjecting the waste material to electron beam radiation utilizing electron energies exceeding $10^7$ electron volts. Commercial linear accelerators are used extensively for the small scale sterilization of surgical bandages and other disposable medical products. However, the use of electron beam energy for the sterilization and treatment of infectious waste material requires a large scale installation with attendant problems relating to costs and occupational safety procedures. For example, the possibility of workers absorbing low level secondary x-ray radiation remains and the disposal of the treated waste requires full secondary storage, transport and final disposition. Moreover, while this method is generally effective in destroying existent pathogens, the penetration efficiency of the electron beam energies diminishes with distance, density and the presence of metallic shielding in the waste material caused by needles, syringes, etc., thus limiting the guarantee of total disinfection of the treated material.

A third type of radiation technology now being used to treat infectious waste material utilizes ultraviolet radiation. However, it has been found that in general, ultraviolet wavelengths are effective only for the surface treatment of the waste materials and therefore, are not appropriate for the processing of infectious waste materials requiring subsurface penetration to accomplish sterilization. This characteristic limits the use of ultraviolet radiation for treating large volume mixed infectious waste.

Processes for eliminating or reducing the concentration of pathogens within waste materials to produce fertilizer materials are known in the art. For example, U.S. Pat. No. 3,953,191 discloses a process for ridding cotton gin waste of detrimental pathogens and weed seeds to produce a fertilizer. This process comprises chopping or grinding the gin waste and steaming the material by the temperature of 215° F. and at constant pressure of 30 psig. U.S. Pat. No. 4,743,287 discloses a method of treating waste organic materials to produce a humic acid base fertilizer formulation which comprises granulating the material and then reacting the granulated material with water, acid and a base. A temperature of about 110° to 280° F. and a pressure of up to 30 psi is maintained in the reaction vessel. Also, U.S. Pat. No. 5,021,077 discloses a method of preparing natural nitrogenous particles useful as plant food by granulating waste material and then heating the material at a temperature of about 50° to 100° C. However, this patent discloses that heating at temperatures higher than 100° C. disadvantageously causes the denaturing of proteins in the material. In contrast to the present method, none of these processes are directed to the treatment of infectious waste.

Accordingly, there is a need for a method for treating infectious waste material to substantially reduce or eliminate the concentration of pathogens therein, which is safe, effective, economical and which produces useful products.

SUMMARY OF THE INVENTION

The present invention has as its objective to provide a method for effectively treating infectious waste material to substantially reduce the concentration of pathogens therein and which results in the provision of useful products. According to the present invention, waste material containing pathogenic microorganisms is processed by a method comprising: granulating the waste material; treating the granulated waste material by heating at a temperature of about 160° to about 200° C., at a pressure of about 90 to about 226 psi in a non-isotonic atmosphere. The granulated waste material is treated for a period of time sufficient to substantially reduce or eliminate the concentration of pathogenic microorganisms in the waste material. After treatment, the treated material is separated into solid and liquid phases. The present invention also encompasses useful liquid fertilizers and industrial composite materials which are products of the present method.

DETAILED DESCRIPTION OF THE INVENTION

Figure 1:
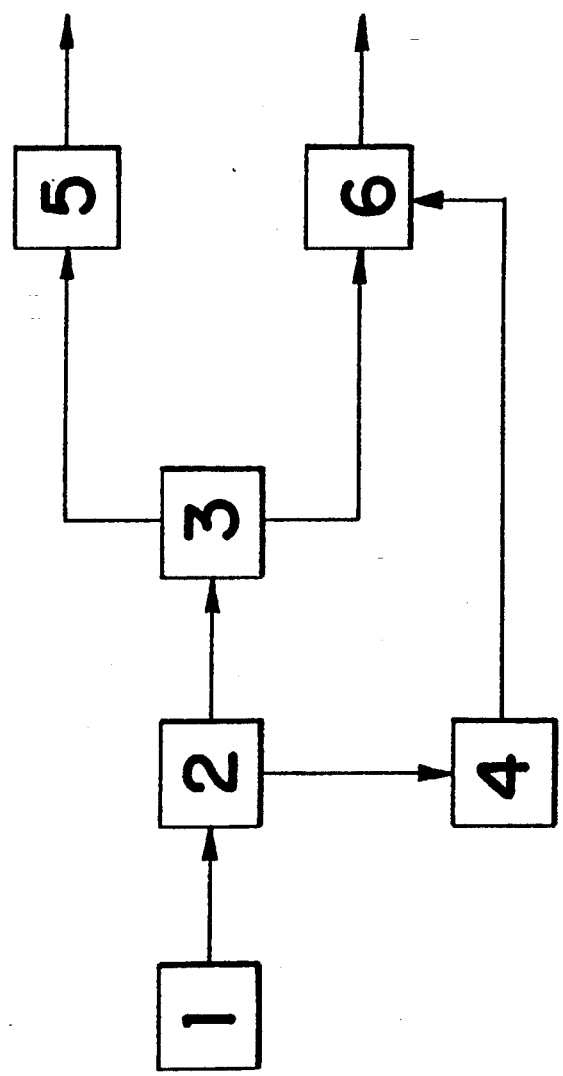
FIG. 1 shows the main steps of the process according to the present invention in diagramatic form.

The present invention is directed to a method for processing and disinfecting waste containing pathogenic microorganisms. More specifically, the present invention is directed to a method for treating infectious waste materials which contain pathogens, such as those found in hospitals, veterinary facilities, and the like, so as to substantially reduce or totally eliminate the amount of pathogenic microorganisms present therein. By "substantially reduce" it is meant that the concentration of the pathogens is reduced to non-detectable levels using conventional assay methods. In many cases, the pathogens are entirely eliminated from the waste. The thus treated material may then be further processed into useful materials, such as liquid fertilizers, industrially useful composite feedstock material, etc.

The pathogenic microorganisms treatable with the present method appear to be unlimited and include all known human pathogenic microorganisms, generally including viruses, bacteria, fungi, protozoa, etc. Specific examples of pathogens which may be treated with the present method include, but are not limited to: *Brucellosis spp., Campylobacter spp., Clostridium spp., diphtheria, Haemophilus spp., Listeria spp., Meningococcus spp., Bordetella spp., Pneumococcus spp., Salmonella spp., Shigella spp., E. Coli, Yersinia spp.,* hepatitis A virus, hepatitis B virus, hepatitis C virus, hepatitis D virus, human immunodeficiency virus (HIV), measles virus, mumps virus, rubella virus, varicella-zoster virus, cytomegalovirus, Epstein-Barr virus, herpes simplex virus type 1, herpes simplex virus type 2, human herpes virus type 6.

Although not wishing to be limited to any particular theory, it is believed that the present method substantially reduces or totally eliminates the pathogenic microorganisms present in the waste material through the specific combination of temperature, pressure and atmosphere used. That is, it is believed that the treatment of the waste material at high temperatures and pressures in the presence of a non-isotonic atmosphere denatures the pathogenic microorganisms by altering their molecular structure so that their outer protective covering is either broken open or altered through osmotic shock and/or biochemical reaction. This acts to either functionally disintegrate the microorganisms and/or structurally alter the genetic information within the microorganisms, so that further multiplication of the pathogens cannot occur. Thus, the original pathogenic entities are broken down to discrete chemical elements, consequently losing their infectious character.

The process for treating infectious waste according to the present invention can best be described with reference to FIG. 1. The main steps of the present process comprises granulating the waste material 1; treating the granulated waste material by heating at a temperature of 160°-200° C. at a pressure of about 90-226 psi in a non-isotonic atmosphere 2; and separating the treated material into solid and liquid phases 3.

In accordance with the present method, the waste material is first mechanically prepared for treatment by granulating the material into particles having a particle size which will facilitate treatment of all of the material with the non-isotonic atmosphere. This is represented by step 1. The particles should be granulated to an extent sufficient to raise the effective surface area of the material to an appropriate degree to allow for the effective processing of all portions of the material. However, generally, the waste material should be granulated into particles having a particle size of about 0.0625 to about 0.25 inches and preferably about 0.0625 to about 0.125 inches.

The granulation step may be carried out by any suitable device known and used in the art which will granulate the material into appropriate sizes. An example of such a device is a Ball and Jewell granulator manufactured by Sterling, Inc. of Milwaukee, Wis. An example of a particularly preferred granulator device useful in the present process consists of knives mounted on rotors which shear the material against knives mounted on the interior walls of a cutting chamber. The size of the particles may be controlled by passing the granulated material through an appropriate base screen upon granulation. The waste material should be granulated for a time period sufficient to process the waste material into fragments and particles of the desired size.

After the granulation step, the granulated waste material is treated by heating at elevated temperatures under high pressures in a non-isotonic atmosphere for a suitable period of time. Such treatment of the granulated waste material may be conducted in a suitable pressure vessel. Appropriate pressure vessels should be prepared in accordance with ASME standards based upon their size and the amount of pressure to be reached in the process. This is represented by step 2 in FIG. 1. Specifically, the granulated waste material is heated at a temperature of about 160° to about 200° C. at a pressure of about 90 to about 226 psi in a non-isotonic atmosphere. This treatment is continued for a period of time sufficient to substantially reduce or totally eliminate the amount of pathogenic microorganisms present in the material to non-detectable levels as determined by conventional assay technology, such as the Infectious Unit Assay method.

The treatment of the granulated waste material includes subjecting the material to temperatures which are sufficiently high to inactivate or destroy pathogenic microorganisms present therein. Generally, it has been found that heating the material at a temperature of about 160° to about 200° C. will accomplish this objective. Heating the waste material at this temperature is also advantageous as it is below levels at which dioxins and other toxic chemicals may be produced from the waste. Preferably, the material is heated at a temperature of about 170° to about 180° C. The heat can be supplied to the reaction chamber by any appropriate means evident to one skilled in the art. However, an example of an appropriate heat generating device is a heater band such as that manufactured by Fast Heat Element Manufacturing Co., Inc. of Elmhurst, Ill.

The treatment of the waste material in accordance with the present method must take place at a pressure which is elevated to a sufficient degree to ensure the destruction of the outer covering of pathogens present in the material. Generally, it has been found that treating the waste material at a pressure of about 90 to about 226 psi will accomplish the stated objective. Preferably the waste material should be treated at a pressure of about 115 to about 146 psi.

In accordance with the present process, the treatment of the granulated waste material at the temperatures and pressures stated above takes place in a non-isotonic atmosphere. That is, the atmosphere in which the waste is treated has a solute concentration which differs from that known to occur within the microorganisms in the waste. This makes the pressure on one side of the cell membrane different from that on the other side creating a pressure differential across the cell membrane. The non-isotonicity of the atmosphere further aids in destroying or altering the protective outer covering of pathogenic microorganisms present in the waste. To accomplish this result, the atmosphere may be either hypertonic or hypotonic with respect to the organisms being treated, but in any event must be non-isotonic with respect thereto.

The atmosphere must be non-isotonic with reference to the microorganisms being treated. The tonicity of the atmosphere is believed to be an important factor in the destruction or alteration of the integrity and infectious nature of the pathogenic microorganisms which require a zero pressure differential across the cell wall membrane to maintain their integrity.

The non-isotonic atmosphere may be generated in any suitable manner evident to one skilled in the art based upon the present disclosure and is not limited. However, it is preferable that the non-isotonic atmosphere comprise the steam from a non-isotonic salt solution. When employing the steam from a non-isotonic salt solution, the atmosphere may be generated, e.g., by loading a hypertonic salt/water solution onto the base of the treatment vessel prior to heating. Once heating is begun within the vessel, the salt/water solution will evaporate causing steam from the salt solution to form. The steam will also be hypertonic, thus providing a non-isotonic atmosphere (i.e., specifically hypertonic) within the reaction vessel.

An alternative method of generating the non-isotonic atmosphere in accordance with the present method utilizes an external high pressure steam generator loaded with a non-isotonic salt solution attached to the treatment vessel. Examples of appropriate steam generators useful in the present method are, e.g., those manufactured by Foster-Wheeler, Inc. of Perryville, N.J. The steam generator injects the treatment vessel with preheated steam arising from the non-isotonic salt solution thus providing the necessary atmosphere. This alternative has advantages in that the steam may be injected at appropriate pressures and temperatures to aid in achieving and maintaining the desired pressures and temperatures within the vessel as discussed above.

The non-isotonic salt solution which is used to form the non-isotonic atmosphere within the treatment vessel in accordance with the above methods may be prepared from any salt which can provide an atmosphere, which is non-isotonic with respect to the pathogenic microorganisms present in the waste. For example, potassium chloride may be used to form the non-isotonic atmosphere. Other salts which are also believed to be effective as a component of the non-isotonic salt solution to produce the non-isotonic atmosphere include the chloride, sulfate, phosphate, nitrate and carbonate salts of potassium, sodium, ammonium, magnesium and calcium. However, it is preferred that potassium chloride, or another salt having plant nutrient properties be used.

The non-isotonic salt solution should contain about 20 to about 30 weight % and preferably, about 25 weight % of the salt. Solutions should be provided which will provide an atmosphere having about 1 to about 7% and preferably about 5%, of the salt. The non-isotonic salt solution may be prepared by any standard procedure which will be evident to one skilled in the art.

In order to insure maximum penetration of the granulated waste material by the non-isotonic atmosphere, it is preferred that the infectious waste material be constantly agitated during the entire treatment period. The agitation of the material may be effected by any appropriate mechanical device evident to one skilled in the art from the present disclosure and is not limited. Examples of appropriate agitation devices are those manufactured by Vibration Products Inc. of Wyoming, R.I.

The granulated material is treated for a period of time sufficient to substantially reduce (i.e., non-detectable levels) or totally eliminate the pathogenic microorganisms within the material. The duration of treatment may vary dependent upon the make-up of the material being treated, particularly the amount of pathogens contained therein and the amount of material being treated. Appropriate treatment durations for specific samples will be evident to one skilled in the art from the present disclosure. However, it is believed that generally, treatment for a time period of about 20 to about 60 minutes, and preferably about 30 minutes, would be sufficient to disinfect a 500 lb. or greater load of waste material and achieve the objectives of the present method.

At the end of the treatment period, the treatment vessel is depressurized. At this time, any accumulated liquids in the treatment vessel may be pumped into a holding tank while the main treatment chamber is opened to allow for the removal of the disinfected, treated waste material. This is represented by step 4 in FIG. 1. These accumulated liquids may be retained for mixture with additional liquids arising from the material due to the further treatment discussed below or may be directly processed as a liquid fertilizer or a component thereof.

As the treatment vessel is depressurized, steam may be generated from the treated material and the treatment system. In order to capture and utilize this steam, a condenser may be attached to the treatment vessel at an appropriate location. The condenser acts to convert the steam to liquid which may then be pumped into the holding tank discussed above and mixed with other liquids arising from the process. As the condensed steam generally contains at least the salt used to form the non-isotonic atmosphere, it is useful in the liquid fertilizer formed by the present method.

The treated waste material is then further processed to effect the separation of the material into solid and liquid phases. This is represented by step 3 in FIG. 1. This separation may be carried out by various suitable devices as will be evident to one skilled in the art from the present disclosure. For example, conventional centrifuge devices may be used to effectively separate the treated material into solid and liquid phases. Examples of appropriate centrifuges are those manufactured by Bird Machine of South Walpole, Mass. This treatment separates the treated material into a solid phase comprising the disinfected solid waste material and a liquid phase generally comprising condensation from the salt-steam atmosphere and an aqueous phase from the waste material comprising highly concentrated organic, inorganic and mineral elements.

The liquid phase may then be removed and combined with the accumulated liquid from the treatment vessel previously removed and discussed above. The combination of the residual liquids may be performed in an appropriate vessel, such as a blender, as will be recognized to one skilled in the art. This is represented by step 6 in FIG. 1. The resulting liquid blend contains a number of valuable plant nutrients, such as the electrolytic component from the non-isotonic atmosphere and/or any residual non-isotonic salt solution and therefore, is useful for direct application to the soil as a liquid fertilizer. The liquid fertilizer thus produced may be used directly in concentrations correlated to a specific fertilizer analysis, or may be blended with other commercial water soluble chemical fertilizers to achieve a target NPK combination liquid fertilizer.

The remaining solid phase may then be safely discarded or further processed. If the material is to be discarded, it can be done so safely without further treatment. The treated solid phase is environmentally safe and non-toxic and thus, may be discarded with conventional waste.

If the solid phase is to be used as an industrially functional composite feedstock product, it may first be dehydrated in order to remove any remaining moisture present therein. The dehydration is represented as step 5 in FIG. 1. Generally, the material should be dehydrated to a moisture content of no more than 10%, although the final moisture content will vary with the ultimate use of the material. The solid phase may be dehydrated in conventional dehydrators or extruders as would be evident to one skilled in the art from the present disclosure. If the solid material is to be dehydrated, it is generally appropriate to attach a scrubber to the dehydration unit in order to remove any odorous organic materials contained therein.

Once dehydrated, the solid material may then be utilized as industrial composite feedstock and processed into any of various articles of manufacture by known extrusion techniques. This solid phase will generally contain variable percentages of polymeric materials, paper, glass, etc., dependent upon the profile of the original waste being treated. Preferably, the dehydrated solid phase material is treated in accordance with Applicant's methods for preparing composite materials which is the subject matter of copending U.S. Patent Application Ser. No. 07/727,176, now U.S. Pat. No. 5,217,655.

Infectious or biomedical waste materials which may be processed with the present method are generally any waste material containing pathogenic microorganisms, such as wastes originating from medical, veterinarian, laboratory and transportation sources which are classified by regulatory bodies as "infectious". The waste material containing pathogenic microorganisms may include mixtures of all types of common waste including plastics, paper, metal, glass, etc. Examples of the type of material contained in the waste created by the present process include plastic and composite paper packaging; plastic and glass tubes; syringes and utensils; aluminum packaging components; hypodermic needles; paper stationery; fabric materials; bedding textiles and fibers; absorbency products (such as diapers and sanitary napkins); disposable paper; composite drapery; bandages; rubber gloves, tubes and other polymeric materials; surplus medical liquids and organic tissue; residual metal fragments from packaging; waste from diagnostic and surgical procedures and cultures; stocks of infectious agents, etc. Generally, the only materials which are presently believed to be unsuitable for treatment with the present method are radioactive and toxic chemicals whose admixture to the waste material to be treated would result in product materials exceeding regulatory safety standards.

The waste material may be treated directly with the present method without the need for presorting. Thus, the present method can be used to treat materials which are specifically packaged in accordance with regulatory guidelines, such as in the form of prescribed coded boxes and plastic pouches, without separation of the packaging from its contents. This provides a unique advantage over conventional methods of treating infectious waste-containing material.

Although the apparatus used to carry out the present process may vary and different appropriate configurations thereof will be evident to one skilled in the art from the present disclosure, it is preferred that the granulator device and treatment vessel be maintained within the same sealed system. That is, the granulator device is preferably maintained inside a sealed vessel designed to insulate the infectious material and associated airborne particles so that no contamination of the external environment can occur. To accomplish this objective, the sealed granulator device should be designed as a subsystem of the total treatment system. Thus, following granulation, the sized particles are transferred to the treatment stage within the same vessel. The entire vessel may thus remain sealed and pressurized during granulation and treatment to ensure disinfection prior to opening the system to reload subsequent batches of waste material therein.

The present invention will now be illustrated with reference to the following specific non-limiting examples.

EXAMPLES

The following examples illustrate the method of the present invention and its efficacy in substantially reducing or totally eliminating the amount of pathogenic microorganisms present in infectious waste material. Each of the examples used the following apparatus.

An apparatus was provided which comprised, as a reaction chamber, a custom pressure vessel designed in accordance with ASME requirements, specifically ASME Boilers and Pressure Vessels Code Section VIII, and which was tested to a maximum pressure of 1200 psi. The reaction chamber was prepared from a stainless steel cylinder having a ½ inch thick wall and a 3.5 inch internal diameter. The cylinder was 10 inches high.

The reaction chamber further comprised a lid which was also prepared from ½ inch stainless steel. The lid was attached to the body of the reaction chamber with eight pressure bolts. A tetrafluoroethylene (TFE) O-ring served as a pressure seal between the lid and the chamber. A heater band manufactured by Fast Heat Element Manufacturing Co., Inc. of Elmhurst, Ill. was attached to the base of the pressure vessel and electrical power was continuously supplied to the heater band.

A pressure gauge was mounted on the lid to allow the continuous monitoring of the pressure within the chamber. A thermocouple was mounted on the lid of the chamber and served as a means of monitoring the temperature within the chamber and also as a controller for the electrical power required to maintain a constant temperature within the chamber. A pressure relief valve was also provided on the lid of the chamber to guard against the accidental over-pressuring of the reaction chamber.

The reaction chamber further comprised a loading basket to hold the test samples. The basket was made from stainless steel screen having a mesh opening of 1/16 inch. The basket had a diameter of 3.5 inches and was 4 inches in height. The basket was attached to a steel ring allowing it to be maintained at the top of the chamber.

Example 1

Example 1 illustrates the efficacy of the present method in inactivating certain representative bacteria, specifically *Bacillus Stearothermophilus* and *Mycobacterium tuberculosis*. These pathogens were chosen due to their high resistance to most conventional decontamination and sterilization procedures. Moreover, it is believed that conditions known to inactivate or destroy these pathogens should also inactivate or render inoccuous virtually all other known pathogens.

Samples B1 to B6 employed a test procedure required by the Canadian Standards (CAN 3-Z314.3-M79) as a sterility test for all steam sterilization processes. According to this procedure, a standard concentration of *Bacillus stearothermophilus* is contained in nutrient media-based solution in sealed glass or plastic containers. These standard samples contain approximately $1.2 \times 10^5$ c.f.u./ml of bacilli. The test vials containing the bacilli were manufactured by Medical Laboratory Systems, 3M Co., Minn. Following incubation at 37° C. for 72 hours, the color change of the nutrient media based solution from purple to any other color indicates the inactivation of the bacilli present in the solution.

In Samples M1 to M6, Mycobacteria was cultured to a concentration of >1000 col./ml in Middlebrook media solution. The cultured solutions were placed in glass Bijou bottles and treated with the present process. After treatment, the samples were tested for the presence of Mycobacteria by a culture test as set forth in the *Manual of Clinical Microbiology*, Ballows A. et al., American Society of Microbiology, Chapter 34 (1991). All samples (B1 to B6 and M1 to M6) were treated in the manner set forth below.

The reaction chamber was first thoroughly cleaned and rinsed with deionized water. The vials containing the pathogens (i.e., Samples B1–B6 and M1–M6) were then placed separately in the treatment apparatus described above. The vials were placed in either the loading basket or on the bottom of the reaction chamber as indicated in Tables I and II. Then, 50 cc of a 25% potassium chloride solution in water was poured onto the bottom of the reaction chamber. The chamber was then heated to a temperature of 160° C. and the pressure within the chamber was maintained at 90 psi. This treatment was conducted for 20 minutes. After 20 minutes, the chamber and its contents were allowed to cool to room temperature and the chamber was depressurized. After treatment, Samples B1–B6 were observed for color change and then were incubated at 37° C. for 72 hours and observed for color change again. After treatment, Samples M1 to M6 were incubated at 37° C. for 21 days. Cultures of each sample were taken after the 21 day period and the concentration of Mycobateria was determined. The results are set forth in Tables I and II below.

TABLE I

| Sample | B1 | B2 | B3 | B4 | B5 | B6 |
|---|---|---|---|---|---|---|
| Container Type | Glass | Glass | Plastic | Plastic | Glass | Glass |
| Initial Color and Turbidity | Clear Purple | Clear Purple | Clear Purple | Clear Purple | Clear Purple | Clear Purple |
| Location in Chamber | Basket | Bottom | Basket | Bottom | Basket | Bottom |
| Color and Turbidity After Treatment | Clear Brown | Hazy Brown | Clear Brown | Hazy Brown | Clear Brown | Hazy Brown |
| Color and Turbidity After Incubation for 72 hours at 37° C. | Clear Brown | Hazy Brown | Clear Brown | Hazy Brown | Clear Brown | Hazy Brown |

TABLE II

| Sample | Control | M1 | M2 | M3 | Control | M4 | M5 | M6 |
|---|---|---|---|---|---|---|---|---|
| Location in Chamber | Basket | Basket | Basket | Basket | Bottom | Bottom | Bottom | Bottom |
| Initial Concentration (colonies/ml) | 0 | >1000 | >1000 | >1000 | 0 | >1000 | >1000 | >1000 |
| Concentration After Treatment | 0 | 0 | 0 | 0 | 0 | 0 | 0 | 0 |

From the results set forth in Tables I and II, it can be seen that treatment of the samples containing both the Bacillus and those containing the Mycobacterium with the present method resulted in the destruction of the pathogens to non-detectable levels. The effectiveness of the present method is clearly evident for both the Bacillus and Mycobacterium species.

Example 2

Example 2 sets forth an actual working example of the present process. The reaction chamber of the treatment apparatus was first thoroughly cleaned and rinsed with deionized water. Then, 50 cc of a 25% potassium chloride solution in deionized water was poured onto the bottom of the reaction chamber.

The base material specified in each of samples P1 to P9 set forth in Table III was pre-granulated to a particle size of 0.25 inches in a Ball and Jewel granulator manufactured by Sterling Inc. of Milkwaukee, Wis. Standard stock solutions of Polio Virus in phosphate buffer saline solution were analyzed in order to determine the concentration (in plaque forming units per milliliter) of Polio Virus present in the solutions. The granulated base material was then innoculated with an amount of the Polio Virus solution appropriate to provide the concentration (pre-treatment) as indicated in Table III. Excess liquid was drained from the granulated base material and the wet, innoculated base material was then placed in the reaction chamber. The material was placed either in the loading basket or on the bottom of the chamber as indicated.

The reaction chamber was then sealed and heated to a temperature of 160° C. and maintained at a pressure of 90 psi. During the entire treatment period, the temperature was maintained within 1° C. and the pressure was maintained within 1 psi. The examples were treated in this manner for 20 minutes.

At the end of 20 minutes, the chamber and the material were allowed to cool to room temperature and the vessel was depressurized. Once cooled, existent residual liquid and the treated solid material were removed from the reaction chamber and separated. The solid material was then washed in a minimal amount of phosphate buffer solution. The washed solution was then combined with the residual liquid earlier removed.

The combined liquid from each sample was then tested by the standard Infectious Unit Assay procedure which is a standard test for viruses of this type. The full procedure is set forth in detail in the *Manual of Basic Virological Techniques.*, G. C. Rovozo and C. M. Burke, Prentice-Hall, pp. 64–93 (1973). The results are set forth in Table III.

TABLE III

| Sample | P1* | P2 | P3 | P4 | P5 | P6 | P7 | P8 | P9 |
|---|---|---|---|---|---|---|---|---|---|
| Initial Conc. PFU/ml | $10^7$ | $10^6$ | $10^8$ | $10^8$ | $10^9$ | $10^9$ | $10^8$ | $10^8$ | $10^7$ |
| Base Material | | 20 g Mixture of Metal/ Plastic/ Paper** | 10 g Mixture of Newspaper and Fiber | 10 g Mixture of Newspaper and Fiber | 10g Mixture of Newspaper and Fiber | 20 g Cloth | 20 g Cloth | Syringes | Syringe |
| Measureable Concentration of Virus After Additon to Base Material | $10^7$ | $10^5$ | $10^6$ | $10^5$ | $10^8$ | $10^7$ | $10^7$ | $10^8$ | $10^7$ |

TABLE III-continued

| Sample | P1* | P2 | P3 | P4 | P5 | P6 | P7 | P8 | P9 |
|---|---|---|---|---|---|---|---|---|---|
| Concentration of Virus in Residual Liquid After Treatment | 0 | 0 | 0 | 0 | 0 | 0 | 0 | 0 | |
| Concentration of Virus in Solids After Treatment | — | 0 | 0 | 0 | 0 | 0 | 0 | 0 | 0 |

*Sample P1 was the control.
**Tetrapak ® Packaging.

As can be seen from the results set forth in Table III, treatment of the granulated waste material innoculated with the Polio Virus results in the destruction of the virus at least to non-detectable levels.

The present invention may be embodied in other specific forms without departing from the spirit or essential attributes thereof and, accordingly, reference should be made to the appended claims, rather than to the foregoing specification, as indicating the scope of the invention.

I claim:

1. A method of processing biomedical waste material containing pathogenic microorganisms comprising:
granulating said waste material;
treating granulated waste material by heating at a temperature of about 160° to about 200° C. at a pressure of about 90 to about 226 psi in a non-isotonic atmosphere comprising solute at a concentration which differs from that known to occur in the pathogenic microorganisms, said atmosphere being generated from a liquid salt solution comprising solvent and solute, for a period of time sufficient to substantially reduce or totally eliminate the amount of pathogenic microorganisms in said material; and
separating said treated waste material from any liquid phase that may be present.

2. A method as in claim 1, wherein said atmosphere is generated from a liquid salt solution which is non-isotonic with respect to said pathogenic microorganisms.

3. A method as in claim 1, wherein said waste material is granulated into particles having a particle size of about 0.0625 to about 0.25 inches.

4. A method as in claim 3, wherein said waste material is granulated into particles having a particle size of about 0.0625 to about 0.125 inches.

5. A method as in claim 1, wherein said granulated waste material is heated at a temperature of about 170° to about 180° C.

6. A method as in claim 1, wherein said granulated waste material is treated at a pressure of about 115 to about 146 psi.

7. A method as in claim 1, wherein said material is treated for a time period of about 20 to about 60 minutes.

8. A method as in claim 7, wherein said material is heated for a period of about 30 minutes.

9. A method as in claim 2, wherein said liquid salt solution comprises a salt selected from the group consisting of chloride, sulfate, phosphate, nitrate, and carbonate salts of potassium, sodium, ammonium, magnesium and calcium.

10. A method as in claim 9, wherein said salt is potassium chloride.

11. A method as in claim 2, wherein said liquid salt solution has a salt concentration of about 20 to about 30 weight %.

12. A method as in claim 11, wherein said liquid salt solution has a salt concentration of about 25 weight %.

13. A method as in claim 2, wherein said atmosphere has a salt concentration of about 1 to about 7%.

14. A method as in claim 13, wherein said atmosphere has a salt concentration of about 5%.

15. A method as in claim 1, wherein said separation of said treated material comprises centrifugation.

16. A method as in claim 1, further comprising dehydrating the separated solid phase.

17. A method as in claim 1 wherein said liquid salt solution is an aqueous solution.

18. A method as in claim 1 further comprising agitating said granulated waste material during said treating step.

* * * * *